United States Patent
Aboul-Hosn et al.

(10) Patent No.: US 7,458,376 B2
(45) Date of Patent: Dec. 2, 2008

(54) SURGICAL DRAPE AND PANEL ASSEMBLY

(75) Inventors: Walid Nalib Aboul-Hosn, Fair Oaks, CA (US); Scott Youmans, Bothell, WA (US)

(73) Assignee: Marquet Cardiovascular, LLC.

( * ) Notice: Subject to any disclaimer, the term of this patent is extended or adjusted under 35 U.S.C. 154(b) by 424 days.

(21) Appl. No.: 11/410,417

(22) Filed: Apr. 25, 2006

(65) Prior Publication Data
US 2006/0191541 A1   Aug. 31, 2006

Related U.S. Application Data

(63) Continuation of application No. 11/058,621, filed on Feb. 15, 2005, now abandoned, which is a continuation of application No. 10/445,639, filed on May 27, 2003, now abandoned, which is a continuation of application No. 09/729,740, filed on Dec. 4, 2000, now abandoned.

(60) Provisional application No. 60/168,795, filed on Dec. 2, 1999.

(51) Int. Cl.
   *A61B 19/00* (2006.01)
(52) U.S. Cl. ........................ 128/849; 128/853
(58) Field of Classification Search .......... 128/849–856
   See application file for complete search history.

(56) References Cited

U.S. PATENT DOCUMENTS

| | | | |
|---|---|---|---|
| 4,664,103 A | 5/1987 | Martin et al. | |
| 5,021,048 A | 6/1991 | Buckholtz | |
| 5,074,316 A | 12/1991 | Dowdy | |
| 5,385,540 A | 1/1995 | Abbott et al. | |
| 5,423,769 A | 6/1995 | Jonkman et al. | |
| 5,558,654 A * | 9/1996 | Hardy | 604/322 |
| 5,573,502 A | 11/1996 | LeCocq et al. | |
| 5,702,358 A | 12/1997 | Witherspoon et al. | |
| 5,707,703 A | 1/1998 | Rothrum et al. | |
| 5,746,575 A | 5/1998 | Westphal et al. | |
| 5,770,149 A | 6/1998 | Raible | |
| 5,840,070 A | 11/1998 | Wampler | |
| 5,849,005 A | 12/1998 | Garrison et al. | |
| 5,899,873 A | 5/1999 | Jones et al. | |
| 5,965,089 A | 10/1999 | Jarvik et al. | |
| 5,970,980 A | 10/1999 | Adair | |
| 5,975,082 A * | 11/1999 | Dowdy | 128/849 |
| 6,036,722 A * | 3/2000 | Augustine | 607/104 |
| 6,123,725 A | 9/2000 | Aboul-Hosn | |
| 6,142,982 A * | 11/2000 | Hunt et al. | 604/313 |
| 6,187,126 B1 | 2/2001 | Rothrum et al. | |
| 6,234,172 B1 * | 5/2001 | Ausbourne et al. | 128/845 |
| 6,309,382 B1 | 10/2001 | Garrison et al. | |
| 6,382,212 B1 * | 5/2002 | Borchard | 128/849 |
| 6,387,323 B1 | 5/2002 | Afzal et al. | |

* cited by examiner

*Primary Examiner*—Michael A. Brown
(74) *Attorney, Agent, or Firm*—Law Office of Alan W. Cannon (57) ABSTRACT

A disposable surgical drape for use in cardiovascular surgical procedures which may optionally be used to isolate a sterile pumping mechanism from a non-sterile pump driving mechanism and/or provide support for medical equipment, such as medical tubing.

8 Claims, 7 Drawing Sheets

SURGICAL DRAPE AND PANEL ASSEMBLY

RELATED APPLICATIONS

This application is a continuation of U.S. patent application Ser. No. 11/058,621 filed 15 Feb. 2005 now abandoned, which is a continuation of abandoned U.S. patent application Ser. No. 10/445,639 filed 27 May 2003, which is a continuation of abandoned U.S. patent application Ser. No. 09/729,740 filed 4 Dec. 2000, which claims the benefit under Title 35, United States Code, §110(e) of U.S. Provisional Application No. 60/168,795 filed on Dec. 2, 1999 and entitled "Surgical Drape and Panel Assembly."

BACKGROUND OF THE INVENTION

I. Field of the Invention

The present invention relates generally to surgical drapes. More particularly, the present invention relates to a disposable surgical drape for use in cardiovascular surgical procedures which advantageously maintains sterile and clean conditions at an operation site and may optionally be used to isolate a sterile pumping mechanism from a non-sterile pump driving mechanism and/or provide support for medical equipment used during cardiovascular procedures.

II. Discussion of the Prior Art

Surgical drapes are well known in the medical community. Generally speaking, surgical drapes are designed to prevent contamination of the sterilized operative site. The need for surgical drapes stems from the inherent risk for infection during surgical procedures. More specifically, bacteria on the patient's skin and/or from unsterilized equipment may infect the surgical site. In order for the bacteria to infect the wound, it must be transferred by a medium such as airborne particles, fluids, lint, dust particles or skin particles originating from the surgeon or patient or any other staff in the operating theatre.

A wide variety of surgical drapes have been developed in the prior art to improve sterility at the operative site. In certain applications, multiple drapes are employed to reduce the possibility of infection, including the use of a surgical drape deployed about the head/neck region of the patient. In this fashion, surgical support staff (such as a perfusionist) may be positioned on the non-surgical side of the drape partition while the surgical team operates within the sterile field on the other side of the surgical drape.

There are two main types of surgical drapes: disposable and reusable. Disposable surgical drapes are typically constructed of multiple layers, with one layer having absorbent properties and another layer that is impervious to fluids. In this fashion, the disposable surgical drape provides both absorbency and a bacterial barrier.

Reusable surgical drapes are typically constructed of cotton fabric. Cotton surgical drapes are advantageous in that, during a surgical procedure, any spilled fluids will be readily absorbed by the drape. As will be appreciated, this eliminates the fluid as a transport medium for bacteria. However, bacteria may nonetheless pass through the fibers forming the cotton drape, and fibers may become detached from the drape, presenting the possibility for bacteria to enter the operative site. To avoid this problem, the drapes have been constructed from a polyester-cotton mixture treated with a liquid repellant finish. While an improvement, these newer cotton-based surgical drapes were nonetheless flawed in that the finish loses its liquid repellant characteristics over time. Another drawback to cotton-based surgical drapes is that they are predisposed to produce lint, which thereby provides a transport medium for the bacteria. Moreover, the production of lint increases after each use and reuse.

During surgical procedures, a second drape may be employed as a partition to separate the sterile surgical site from a non-sterile zone outside the field of surgery. When deployed about the patient's head and/or neck, such a drape is referred to as an "anesthesiologist screen" because it separates the non-sterile area where the anesthesiologist sits during surgery from the sterile surgical area below the patient's head and neck. Anesthesiologists typically monitor and seek to control such patient characteristics as blood gas, lung ventilation, body temperature, and evacuation of fluids.

In cardiopulmonary bypass (CPB) procedures, the anesthesiologist is also responsible for establishing and monitoring the bypass circuit. CPB surgery involves the use of a blood pump to remove and return blood from the patient's body through cannulas and tubing placed within the patient's circulatory system. The outflow cannula is connected to a blood pump, such as the one disclosed in U.S. Pat. No. 5,746,575 titled "Blood Pump as Centrifugal Pump," the disclosure of which is hereby expressly incorporated by reference. The blood pump is driven through the use of a motor that is magnetically coupled to the blood pump. Typically, the motor used to drive the blood pump is not sterilizable such that the motor must be positioned outside the sterile surgical field. By placing the blood pump and motor outside the sterile field, long lengths of surgical tubing must be utilized to connect the blood pump to the cannula. This additional medical tubing increases the priming volume of the CPB circuit and may also increase hemolysis based on the exposure to a greater amount of foreign surface area, i.e. the tubing.

To establish a CPB circuit, medical tubing is passed from the sterile surgical site, under the anesthesiologist screen, for connection to the blood pump and motor driving unit located in the non-sterile region. The anesthesiologist must de-air the system to ensure no air emboli will form in the patient's blood system. After de-airing the system, the tubing is connected to a blood pump, which the anesthesiologist controls with an associated pump control and monitoring system. Throughout the entire procedure, the surgeon must relay control commands to the anesthesiologist and rely upon these communications. The surgeon is typically unable to view the pump or control panel at any time during the procedure.

The CPB circuit described above, while very common in use, is nonetheless flawed in several significant ways. First, this prior art CPB circuit is undesirable because it increases the amount of foreign material that the blood is in contact with, thereby increasing the likelihood of hemolysis. This is due to the need to place the blood pump and motor outside the sterile surgical field. The blood must also be further treated with heparin to reduce the natural clotting that occurs as the result of contact between the blood and the foreign material of the CPB circuit. Another significant drawback of the CPB system of the prior art is that the pump and motor are necessarily placed outside the sterile surgical field (due to the inability to sterilize the motor). With the pump and motor outside sterile surgical field and thus outside the surgeon's field of view, a second person must be present within the operating room to monitor and control the pump and driving motor. This disadvantageously clutters the operating room. Moreover, the information displayed on the CPB equipment must be relayed to the surgeon, thereby further complicating the procedure.

The present invention is directed at overcoming, or at least reducing the effects of, one or more of the problems set forth above.

SUMMARY OF THE INVENTION

The present invention addresses the shortcomings of the prior art surgical drapes by providing a sterile barrier having a support panel particularly adapted for use in cardiovascular procedures. The surgical drape and panel assembly advantageously provides the ability to position a sterile blood pump within the sterile surgical field, thereby reducing the CPB circuit and freeing up valuable space around the head and neck region of the patient. This allows the perfusionist more room to perform their work.

The present invention generally relates to a surgical drape having a mechanism for disposing a blood pump therethrough or about. The surgical drape has defined sections, which allow the surgeon to pass a sterile pump drive cable therethrough, thereby isolating the non-sterile driving mechanism (i.e. motor) from the sterile pump assembly located within the surgical field. Further, the drape may include areas specifically designed to be placed between the coupling between the sealed pumping mechanism and the driving motor.

By utilizing the present invention, the surgeon may place the sterile pump closer to the surgical site, thereby reducing the amount of foreign tubing that is necessary to connect the blood pump to the cannulas placed within the patient's vascular system. A further advantage of the invention is that the pump, driving mechanism, and control panel may be located at a distance closer to the surgeon, thereby enabling the surgeon to view the information more readily. The driving mechanism and control panel may be located near the patient's head, thereby allowing the perfusionist closer monitoring of the pump system and the patient's vital signs.

In one embodiment of the present invention, the surgical drape is designed such that it is to be disposed adjacent to the patient's head region. The surgical drape is sufficiently thin so as to allow the surgeon to couple a sterile blood pump to a non-sterile driving mechanism without interfering with the clamping mechanism.

In another embodiment the surgical drape further contains apertures which allow sterile materials to be passed through from the surgical site, to the non-sterile surgical site adjacent to the patient's head area. Thereby allowing a sterile pump to be placed closer to the surgical site while the non-sterile driving mechanism is placed outside the sterile surgical field. Thus further reducing the amount of foreign tubing used to connect the blood pump to the patient's vascular system.

In another embodiment, the surgical drape further comprises a rigid panel disposed about the head/neck region of the patient, whereby the panel is adapted to receive a blood pump and associate tubing during a surgical procedure.

In another embodiment the surgical drape of the present invention further comprises a clear viewing portion thereby allowing the surgeon/anesthesiologist look through the drape instead of having to move around the drape.

In another embodiment, the rigid panel structure further contains connectors for various medical devices utilized during a surgical procedure. Thus, by utilizing the panel and the connections contained thereon the surgeon is better able to organize the surgical field.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from on implementation to another. Moveover, it will be appreciated that such a development effort might be complex and time-consuming, but would nevertheless be a routine undertaking for those of ordinary skill in the art having the benefit of this disclosure.

Referring now to the drawings, there is shown a preferred embodiment of a surgical drape in accordance with the present invention. The drape is particularly suited for use during cardiovascular procedures where a blood pump is utilized or for any other surgical procedures utilizing coupled devices that consist of sterile and non-sterile portions.

Figure 1:
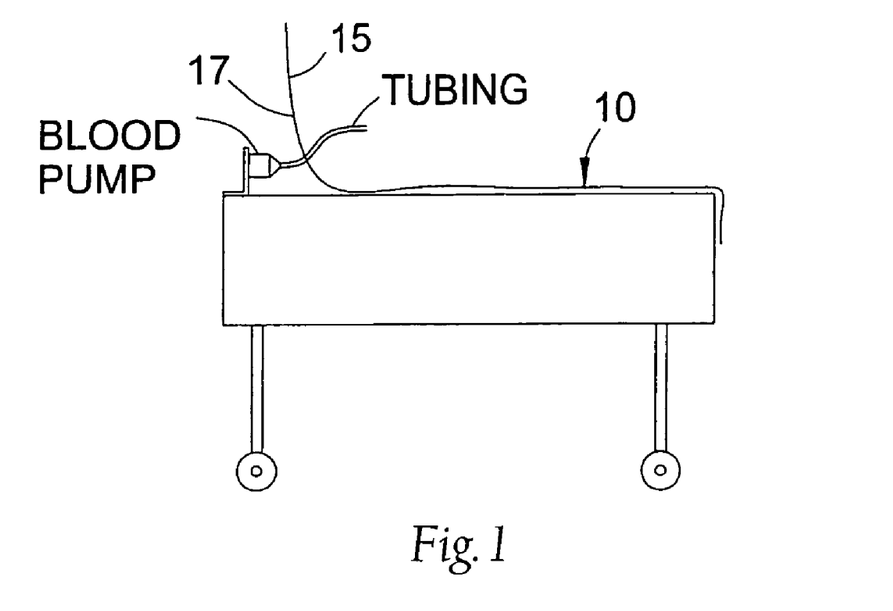
FIG. 1 is an illustration of the surgical drape of the present invention.

As illustrated in FIG. 1, surgical drape 10 is generally rectangular and is formed of a flexible material of sufficient size such that surgical drape 10 may be utilized as a screen between the surgical field and the anesthesiologist. Surgical drape 10 comprises of first surface 15 and second surface 17. During use, first surface 15 is disposed facing the sterile surgical zone and second surface 17 faces the non-sterile area.

Figure 2:
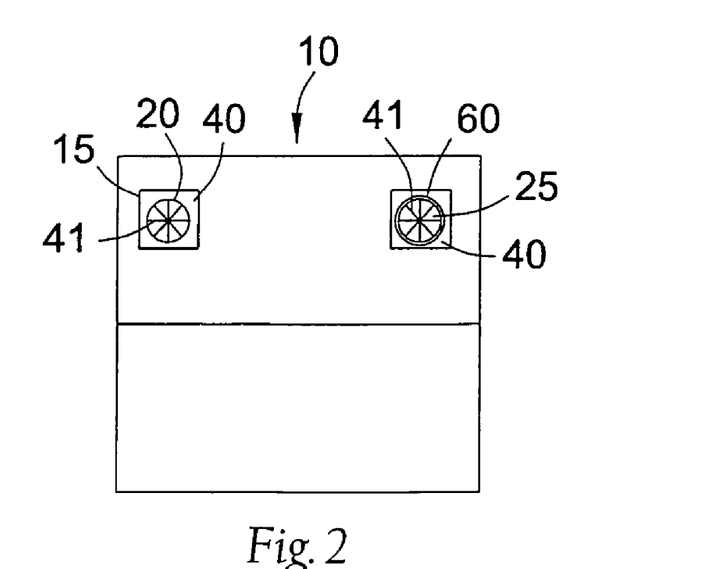
FIG. 2 is a front view of the surgical drape.
Figure 3:
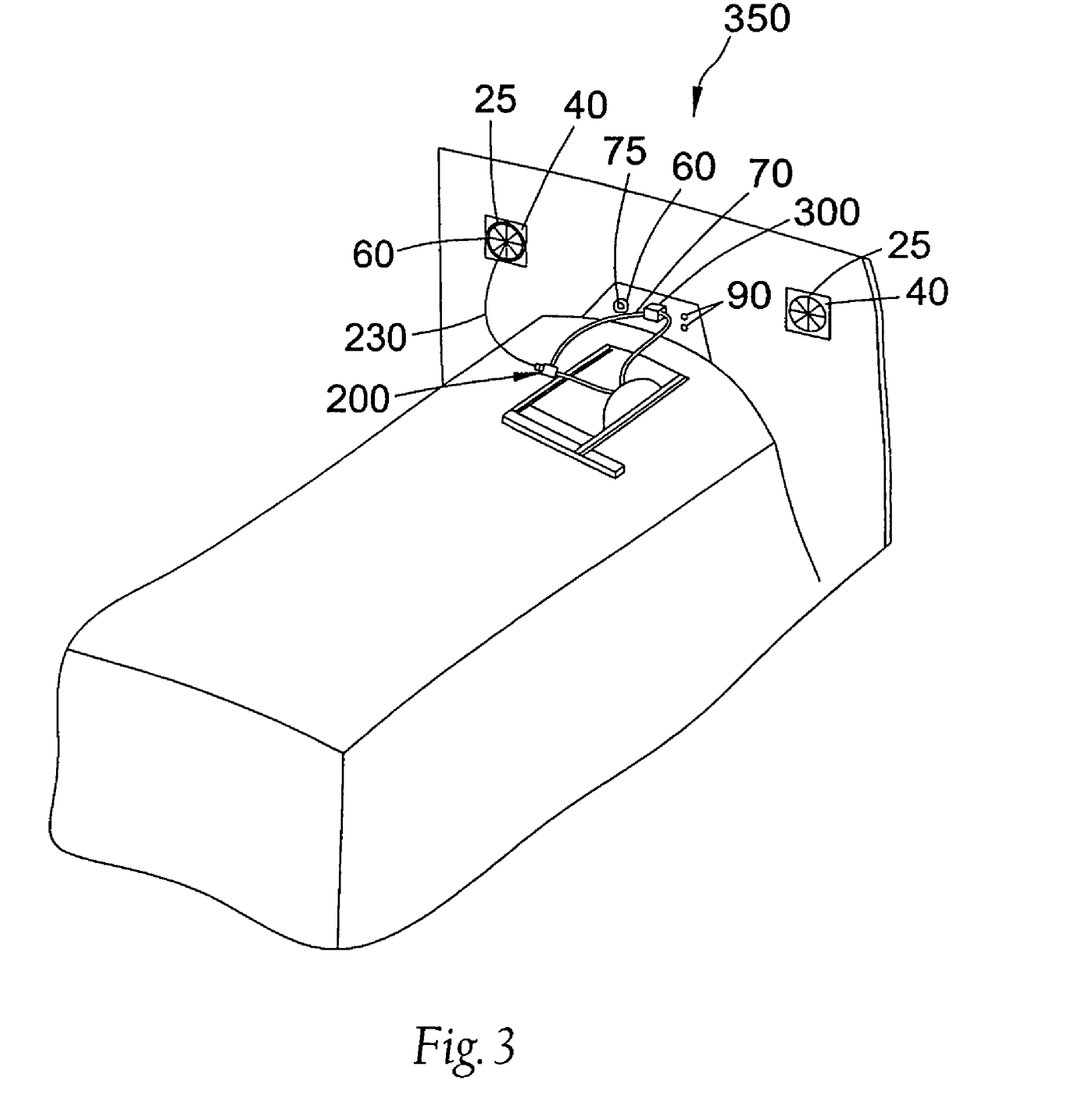
FIG. 3 is a perspective view of the surgical drape and panel of the present invention.
Figure 4:
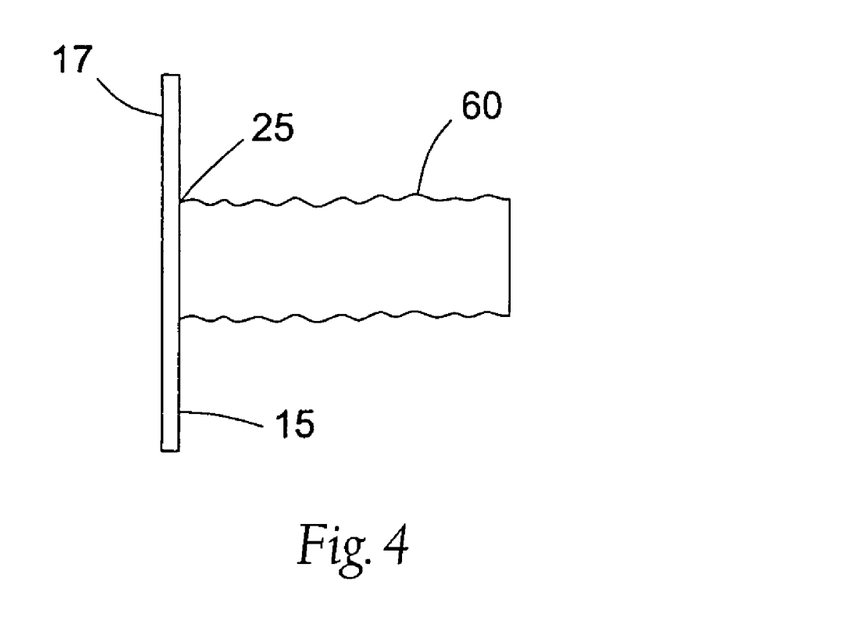
FIG. 4 is a side view of the panel/drape of the present invention.

As illustrated in FIGS. 2 and 3, surgical drape 10 may further contain aperture(s) 25 disposed therethrough. In use, aperture 25 may be used to pass surgical devices through the drape from the sterile surgical side to the non-sterile area. As illustrated in FIG. 1, the physician can pass tubing through aperture 25, which may then be connected to a blood pump located outside the sterile field. Alternatively, as shown in FIG. 3, a sterile pump drive cable 230, can be passed through aperture 25 and connected to a motor (not shown) within the non-sterile surgical field and a pump 200 located within the sterile surgical field.

As shown in FIG. 2, aperture 25 may further contain a sterile sleeve 60, which may be disposed about a medical device that is passed through the aperture 25. The sterile sleeve 60 may by utilized where a sterile device has been passed through to the non sterile side, thereby rendering it non-sterile, though at some time during the procedure it may be necessary to move the device from the non-sterile side back into the sterile surgical field. In order to do so, sleeve 60 may be disposed about the device so that the non-sterile device is encapsulated within the interior of sleeve 60. Therefore, the non-sterile device may be brought back into the sterile surgical field because the sleeve 60 protected the device from contamination while in the non-sterile field.

As illustrated in FIG. 2, aperture 25 and sleeve 60 are initially covered by membrane 40, which is attached to the first surface 15 or second surface 17 of drape 10. Membrane 40 may be disposed about aperture 25 such that membrane 40 reinforces the edges of the aperture 25. This reinforcement provides further protections against tearing or abrasion about aperture 25 and drape 10. Prior to using aperture 25, the user must first open aperture 25 by tearing the perforations 41 that are disposed within the surgical drape 10. The perforations 41 facilitate the controlled tearing of the drape when desired.

Surgical drape 10, which may compromise any flexible disposable woven, non-woven, or plastic material, has a first surface 15 and second surface 17. As used within this disclosure, it should be understood that the second surface 17 will be in contact with the patient's body if drape 10 is utilized to cover the patient's body during surgical procedures. Alternatively, if drape 10 is utilized as a screen between the patient's body and the anesthesiologist/perfusionist, then it should be understood that the second surface 17 will be facing the anesthesiologist as illustrated in FIG. 1, while the first surface 15 of drape 10 will face away from the anesthesiologist. Drape 10 is preferably constructed of a non woven material which has been treated to make it repellent to liquids such as water, alcohol, blood, saline, or any other fluid that may be encountered during a surgical procedure. Surgical drape 10 may be formed of a single piece of material or may be formed of a plurality of pieces that are permanently bonded together. Alternatively, the surgical drape of this invention may be formed of multiple layers.

Figure 5:
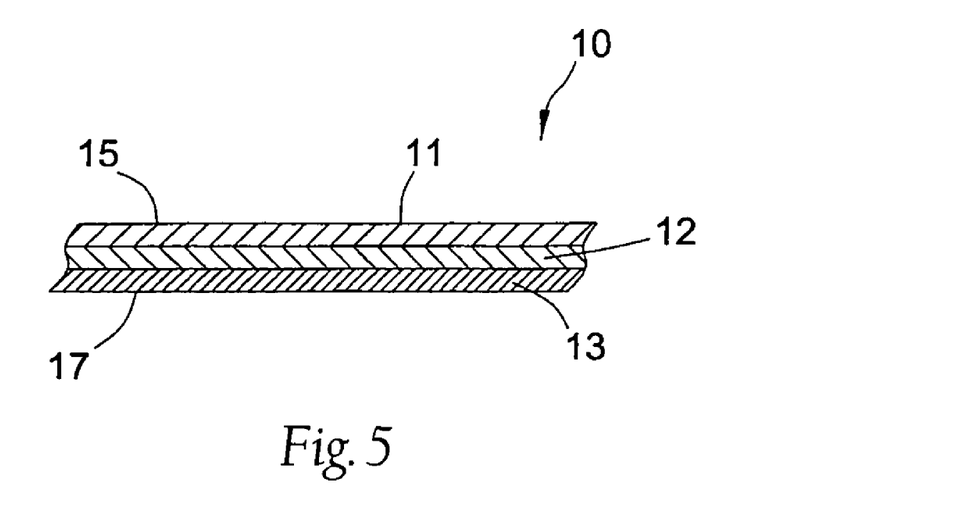
FIG. 5 is a cross-sectional view of the surgical drape of the present invention.

As shown in FIG. 5, the first layer 11 is permeable and allows fluid to pass therethrough. The second layer 12 is constructed of an absorbent material which absorbs the fluid that is allowed to pass through the first layer 11. The third layer 13 is constructed of an impervious material, therefore any fluids that come into contact with the drape during a surgical procedure will be absorbed by the second layer 12 of the drape 10 and not contact the skin of the patient. Alternatively, the surgical drape 10 of the present invention may be formed of two layers (not shown). An upper absorbent layer 12 and a lower impermeable layer 13 thereby lessening the cost of manufacture and the overall bulk of the drape.

As illustrated in FIGS. 1 and 3, in use, surgical drape 10 may be utilized as a screen between the head and neck region of the patient. As mentioned previously, surgical drape 10 is particularly suited for use in cardiovascular procedures and is preferably sufficiently long, not only to be utilized as an anesthesia screen but also to cover the body of the patient. As illustrated in FIG. 3, a sterile blood pump 200 may be placed within the sterile operating field while the flexible drive 230 cable is passed through the aperture 25 and connected to a motor 250 (not shown) disposed on the non-sterile side. This arrangement is particularly useful in that it allows a sterile pump to be placed within the surgical field, thereby lessening the priming volume of the bypass circuit.

Figure 6:
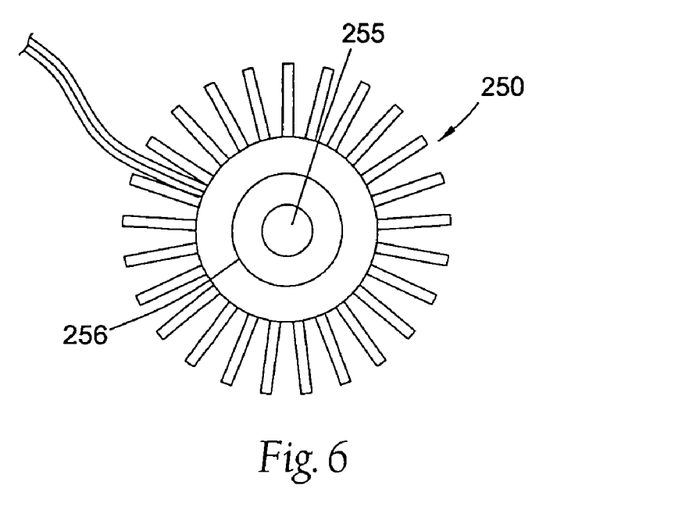
FIG. 6 is a top view of the motor.
Figure 7:
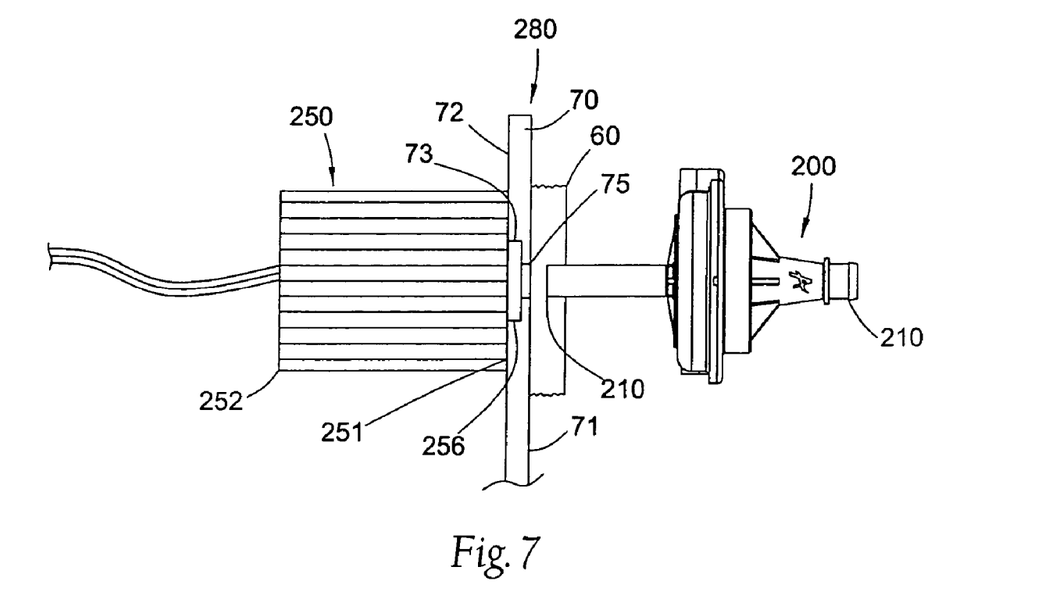
FIG. 7 is a side view of the panel illustrating the pump and motor of the present invention.

With combined reference to FIGS. 3 and 8-10 surgical drape 10 may further comprise panel 70. Panel 70 is adapted to be disposed adjacent to or about the patient's head during surgical procedures. Panel 70 is adapted to receive and retain a blood pump 200, a blood reservoir (not shown), a blood filter (not shown), or a blood oxygenator 300, either singly or in any combination thereof. As shown in FIGS. 6 and 7, blood pump assembly 280 comprises a sterile pump 200 and a non-sterile motor 250. The non-sterile motor 250 contains bore 255 dimensioned to receive the sterile pump 200.

As shown in FIG. 7, panel 70 contains annular groove 73 dimensioned to receive coupling member 256. Coupling member 256 extends from the first end 251 of motor 250 and is dimensioned to be received within annular groove 73 of panel 70 and align bore 255 of motor 250 and aperture 75 of panel 70. When assembled, motor 250 is adjacent second surface 72 of panel 70, thereby isolating the non-sterile motor 250 from the sterile surgical field. In use, the distal end 210 of the pump 200 is inserted through aperture 75 of panel 70 and bore 255 of motor 250. Panel 70 may further comprise a sterile sleeve 60 disposed about aperture 75. If the sterile pump 200 must be removed and placed within the non-sterile field, sleeve 60 is disposed about sterile pump 200. The sleeve 60 protects the sterile pump 200 from contamination within the non-sterile field, thereby allowing the pump 200 to be replaced within the sterile field after removal.

Figure 8:
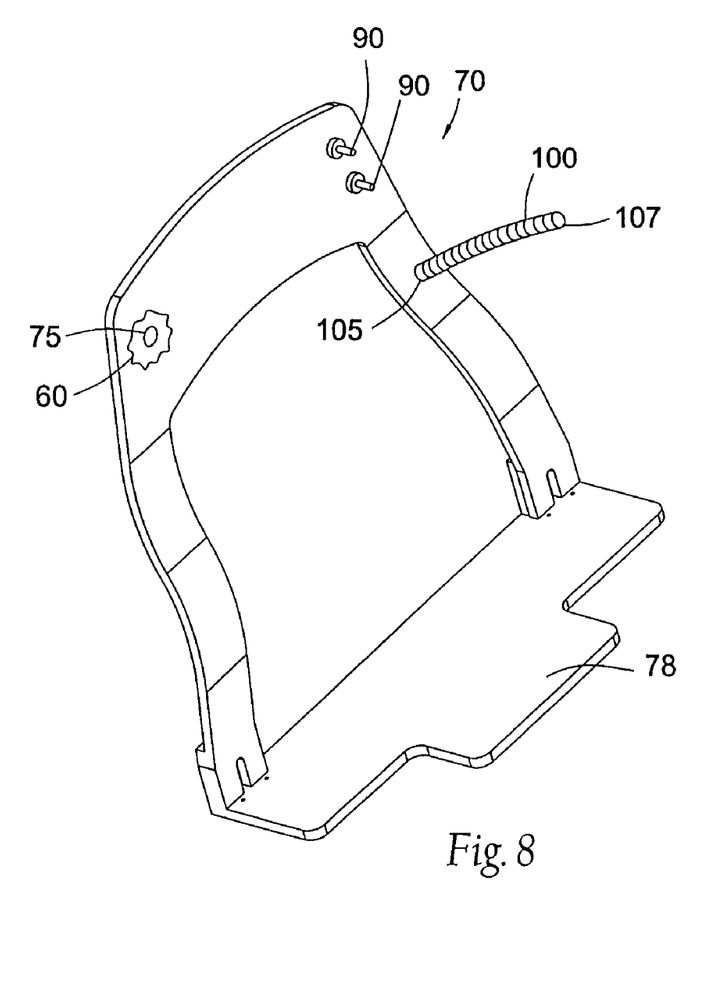
FIG. 8 is a perspective view of the panel of the present invention.

In an alternative embodiment illustrated in FIG. 8, panel 70 may further contain fittings 90. One such use for fittings 90 is to make a connection between a blood suction/cell saver apparatus and the surgical field. Or fittings 90 may be utilized to supply compressed carbon dioxide, oxygen, or saline to the sterile surgical site. These exemplary illustrations should not be construed as to limit the function of the fittings 90. Fittings 90 may be utilized for many other applications not illustrated. As shown in FIG. 8, panel 70 may further comprise flexible arm 100 having a first end 105 and a second end 107. The first end 105 of arm 100 is adapted to be received by panel 70. The second end 107 of arm 100 is adapted to receive a surgical device. Arm 100 is sufficiently stiff therefore allowing the surgeon to adjust the location of the second end 107 of the arm 100 relative to the surgical site. As illustrated in FIG. 8 panel 70 may be attached to panel support 78. Panel support 78 is adapted to be inserted under the patient's shoulders and to receive panel 70, thereby disposing panel 70 about the patient's neck and head region.

Figure 9:
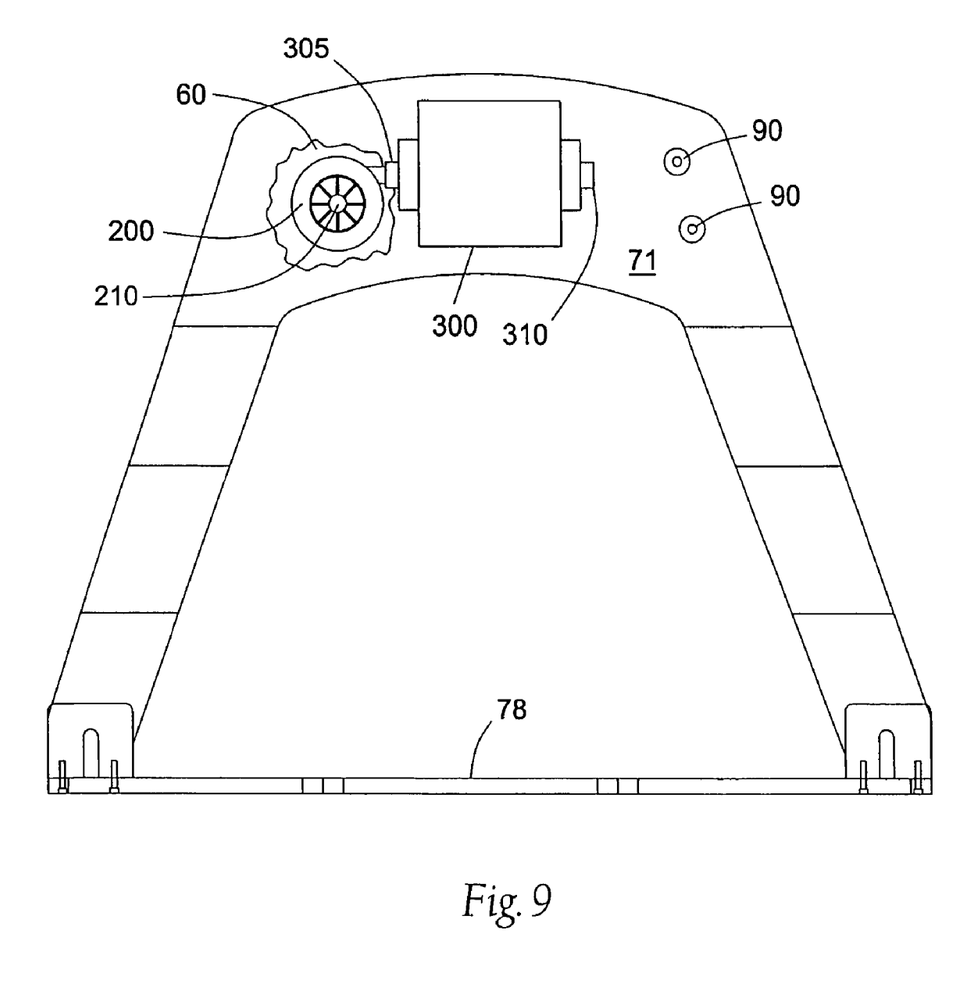
FIG. 9 is a front view of the panel of the present invention.

As shown in FIG. 9, panel 70 may further. comprise oxygenator 300 coupled to first surface 71 of panel 70. Oxygenator 300 comprises fluid inlet 305 and fluid outlet 310. Fluid inlet 305 is in fluid communication with pump 200, thereby providing a compact bypass circuit within the sterile surgical field. Panel 70 provides a further benefit by moving the pump 200 and oxygenator 300 off of the surgical table, thereby freeing valuable space within the surgical field. An additional benefit of the arrangement as shown is that the surgeon may easily view the bypass circuit at any time during the procedure.

Figure 10:
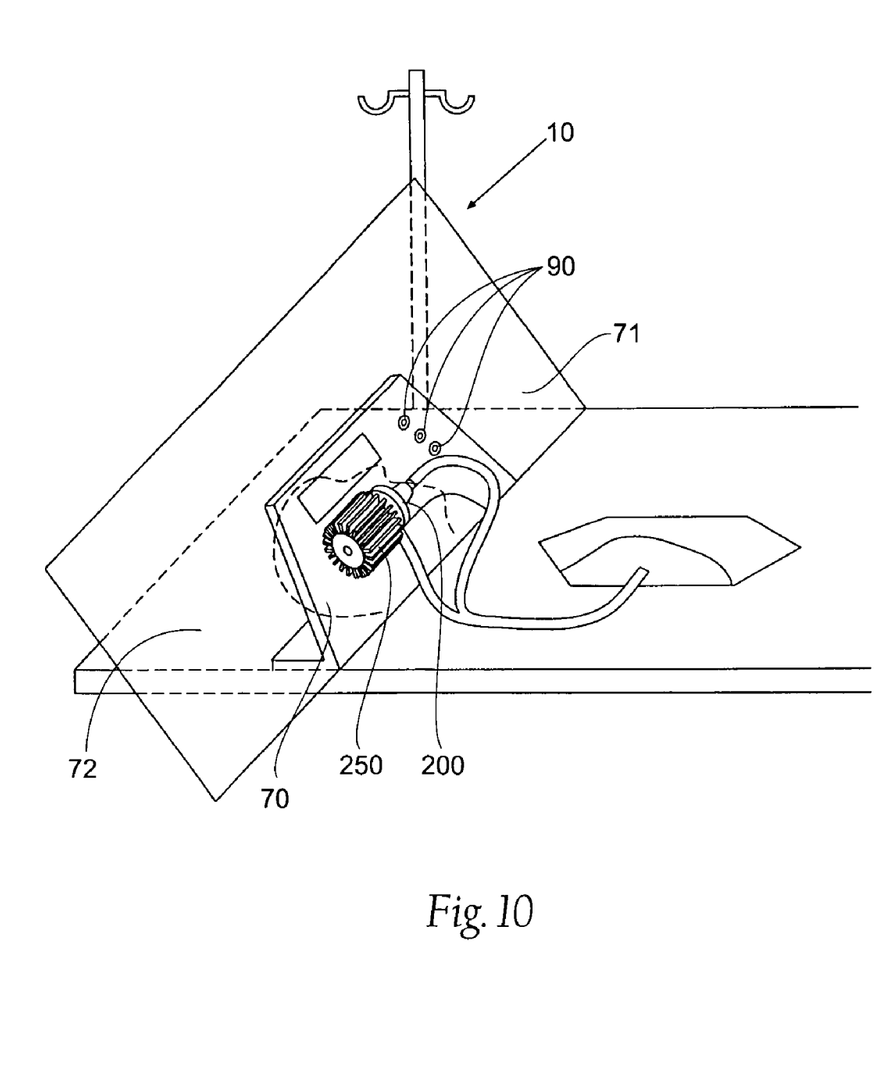
FIG. 10 is a perspective view illustrating various features of the present invention.

As shown in FIGS. 3, 9-10, drape 10 may be coupled to panel 70 thereby providing an assembly 350 that separates the sterile field from the non-sterile field. Assembly 350 allows pump 200, oxygenator 300, and other medical devices to be placed within the sterile surgical field thereby decreasing the overall priming volume of the bypass circuit. Assembly 350 further allows materials and/or devices to be passed between the sterile field and the non-sterile field. Panel 70 is constructed of a biocompatible material such as plastic or metal. In one embodiment, panel 70 is manufactured of a transparent or semi-transparent material, thereby allowing the perfusionist/anesthesiologist or surgeon to see through the panel.

While this invention has been described for use in cardiovascular surgery, this does not limit the applications of this invention for the use cardiopulmonary bypass surgery only. The invention herein disclosed can be utilized in other applications apparent to those skilled in the art.

It will be apparent by those skilled in the art that changes could be made to the embodiments described above without departing form the broad inventive concepts thereof. It is understood, therefore, that this invention is not limited to the particular embodiments disclosed, but is intended to cover modifications within the spirit and scope of the present invention as defined by the appended claims.

We claim:

1. A surgical drape assembly, comprising:
   a sterile pump assembly including a non-sterile driving mechanism coupled to the pump assembly by a sterile pump drive cable,
   a surgical drape having at least one aperture dimensioned to allow the sterile pump drive cable to pass therethrough so as to isolate the non-sterile driving mechanism from the sterile pump assembly located within the surgical field; and
   a panel structure coupled to said surgical drape adapted to support at least one of said sterile pump assembly and said non-sterile driving mechanism.

2. The surgical drape assembly of claim 1 and further, wherein said panel structure is further adapted to support a display for displaying information to surgical personnel.

3. The surgical drape assembly of claim 1 and further, wherein said panel structure is further adapted to support at least one of a suction port coupled to a suction source and a pressure port coupled to a pressure source.

4. The surgical drape assembly of claim 1 and further, wherein the panel structure is adapted to support a gas port coupled to a least one of an oxygen source and a carbon dioxide source.

5. The surgical drape assembly of claim 1 and further, wherein said surgical drape is constructed from a generally transparent material.

6. The surgical drape assembly of claim 1 and further, wherein said panel structure is dimensioned to be positioned between the head and neck region of the patient and the torso region of the patient.

7. The surgical drape assembly of claim 1 and further, wherein said panel structure is adapted to support at least one of an oxygenator and a fluid reservoir forming part of a cardiopulmonary bypass circuit.

8. A method of isolating a sterile blood pump disposed within the sterile surgical field from a non-sterile motor disposed outside the sterile surgical field, comprising the steps of:
   (1) positioning a surgical drape and panel assembly such that a panel structure is positioned between the head and neck region of the patient and the torso region of the patient;
   (2) coupling said sterile blood pump to the side of the panel structure facing the torso region of the patient such that the sterile blood pump is disposed within the sterile surgical field; and
   (3) coupling said non-sterile motor to the side of the panel structure facing the head and neck region of the patient such that the motor is disposed outside the sterile surgical field.

* * * * *